United States Patent [19]

Carter, Jr. et al.

[11] Patent Number: 4,590,063
[45] Date of Patent: May 20, 1986

[54] ANTICONVULSANTS

[75] Inventors: John P. Carter, Jr., Columbus; Richard L. Wolgemuth, Plain City, both of Ohio

[73] Assignee: Adria Laboratories, Inc., Columbus, Ohio

[21] Appl. No.: 727,048

[22] Filed: Apr. 25, 1985

Related U.S. Application Data

[62] Division of Ser. No. 507,620, Jun. 24, 1983, Pat. No. 4,540,814.

[51] Int. Cl.$^4$ ............ A61J 3/06; A61K 9/14; A61K 9/16; B32B 5/16
[52] U.S. Cl. .......... 424/19; 424/20; 424/35; 514/622; 514/650; 514/781; 514/963; 514/964; 428/402.2; 428/402.24
[58] Field of Search ............ 424/19, 20, 35; 514/613, 622, 650, 781, 963, 964; 428/402.2, 402.24

[56] References Cited

U.S. PATENT DOCUMENTS

| | | | |
|---|---|---|---|
| 3,155,590 | 11/1964 | Miller et al. | 424/35 |
| 4,059,621 | 11/1977 | Vincent et al. | 544/106 |
| 4,150,153 | 4/1979 | Walker | 548/336 |
| 4,275,071 | 6/1981 | Nardi et al. | 548/335 |
| 4,277,486 | 7/1981 | Walker | 548/336 |
| 4,293,561 | 10/1981 | Walker | 548/336 |
| 4,316,884 | 2/1982 | Alam et al. | 424/35 |

OTHER PUBLICATIONS

Fieser, L. F., *J. Amer. Chem. Soc.*, vol. 70, pp. 3165-3174, 1948.

Primary Examiner—John Kight
Assistant Examiner—Nathan M. Nutter
Attorney, Agent, or Firm—Marion C. Staves

[57] ABSTRACT

Compounds of the formula

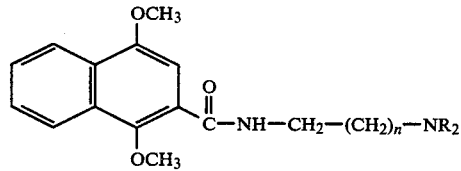

where R is a methyl, ethyl or propyl group and n is 1 or 2 and their nontoxic salts are useful as anticonvulsants.

6 Claims, No Drawings

ANTICONVULSANTS

This application is a division of application Ser. No. 507,620, filed June 24, 1983, and now U.S. Pat. No. 4,540,814.

FIELD OF THE INVENTION

This invention relates to novel compounds, the synthesis of said compounds and their use in treating grand mal epilepsy. More particularly, this invention relates to novel naphthalene carboxamides and their nontoxic salts, their synthesis from 1,4-dimethoxynaphthalene and their use in treating convulsions and seizures resulting from epilepsy.

BACKGROUND OF THE INVENTION

Epilepsy is a disease, which has been known for a long period of time, causing seizures and convulsions. There are various drugs on the market for the treatment of epilepsy; however, unfortunately, many of the present drugs cause serious side effects or are toxic. One drug now used in the treatment of epilepsy is phenytoin (Dilantin). Dilantin is effective in preventing seizures and convulsions caused by epilepsy; however, it has serious chronic side effects such as megaloblastic anemia and osteomalacia. Another well known drug for the treatment of epilepsy is valproic acid. This compound, unfortunately, must be given in large dosages to be effective; in fact, dosages very close to those which are acutely toxic.

SUMMARY OF THE INVENTION

It has now been found that certain 1,4-dimethoxynaphthalenecarboxamides and their nontoxic salts are highly effective in the treatment of seizures and convulsions caused by epilepsy, while at the same time exhibiting low acute toxicity and possessing few side effects. The therapeutic compounds of this invention are 1,4-dimethoxynaphthalenecarboxamides having the general formula

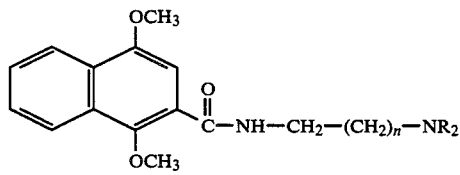

wherein R is selected from methyl, ethyl and propyl groups and n is either 1 or 2 and their nontoxic salts.

DETAILED DESCRIPTION OF THE INVENTION

As indicated above, the novel therapeutic compounds of this invention are 1,4-dimethoxynaphthalenecarboxamides and their nontoxic salts having the general formula shown above. Typical nontoxic salts are the acid salts, as for example, the tartrate, bitartrate, acetate, citrate, maleate, malate, methane-sulfonate, sulfate, phosphate, hydrochloride, hydrobromide and the like. These compounds can be easily synthesized starting from the known compound 1,4-dimethoxynaphthalene. The dimethoxynaphthalene can be prepared by the method of L. Fieser, *Journal of the American Chemical Society*, Volume 70, pages 3165 (1948).

The process of preparing the novel compounds of this invention comprises the steps of (1) brominating 1,4-dimethoxynaphthalene with liquid bromine in an organic solvent such as acetic acid at room temperature to form the 2-bromo-1,4-dimethoxynaphthalene, (2) converting the bromine derivative to the carboxylic acid derivative by lithiation and carboxylation. The lithiation is conducted in a known procedure, as for example, by treating the bromo derivative with n-Butyllithium in an organic solvent under anhydrous conditions at a low temperature, such as $-78°$ C. The resulting lithium compound is not isolated, but converted into the carboxylic acid by adding dry ice to the cooled lithium compound and allowing the reaction mixture to come to room temperature. (3) The carboxylic acid derivative is then converted to the acid chloride by treating with thionyl chloride at room temperature. (4) The resulting acid chloride is condensed with the appropriate amine to form the carboxamide. The condensation reaction is carried out by treating the acid chloride in an organic solvent with the appropriate amine at room temperature in the presence of a proton acceptor.

The compounds of this invention are particularly effective in suppressing grand mal convulsions and psychomotor seizures caused by epileptic disorders. In order to suppress seizures or convulsions, the compounds of this invention can be administered by any acceptable pharmaceutical route, such as intramuscularly, subcutaneously, intravenously or orally. Most preferably, the compounds will be administered orally by tablet or capsule containing about 25 to about 200 mg of the compound. Normal dosages for humans will be from about 1 to about 50 mg per kilogram, most probably about 10 to about 30 mg per kilogram of body weight, administered in multiple daily dosages. To avoid the multiple daily dosages, it may be desirable in certain cases to microencapsulate the compounds or to compound them in the form of spansules, which take effect over a longer period of time. The microencapsulation of these compounds is carried out in accordance with normal procedures known to those skilled in the art such as shown in U.S. Pat. Nos. 4,316,884 and 3,155,590 the disclosures of which are incorporated herein by reference. Slow release oral administration may be the most desired method of administration, although the other methods disclosed above are quite acceptable.

The compounds of this invention are solids having a low toxicity and high safety ratio. Compounds of this invention have an approximately $LD_{50}$ of around 750. In other words, it requires approximately 750 mg per kilogram of body weight to kill 50% of the animals administered the drug. The compounds, in addition, have a low $ED_{50}$. In other words, only a small amount of the compound is required to suppress convulsions or seizures in 50% of the animals treated. The approximate safety ratio of the compound is determined by dividing the $LD_{50}$ by the $ED_{50}$, which in the case of the instant compounds, is relatively high. Thus, larger amounts of the instant compounds can be administered to patients in need of such treatment without concern that the compounds will be toxic.

In preparing medicaments using the compounds of this invention, it is possible to mix the compounds with the normal additives, excipients, etc. used in preparing a pharmaceutical composition, such as pregelatinized starch, lactose, or the like.

The following examples will serve to illustrate the instant invention. Parts and percentages are by weight unless indicated otherwise.

EXAMPLE 1

This example illustrates the preparation of a typical 1,4-dimethoxynaphthalenecarboxamide.

To a solution of 50 grams (0.26 mol) of 1,4-dimethoxynaphthalene, prepared according to the procedure of L. Fieser, in the *Journal of the American Chemical Society*, Volume 70, page 3165 (1948), in 500 ml glacial acetic acid is added 13.7 ml (0.26 mol) of bromine at room temperature. The mixture is stirred for 1 hour, and the solvent is removed under reduced pressure and the residue dissolved in ether. The resulting solution is carefully washed twice with sodium bicarbonate, the organic layer separated, dried over sodium sulfate and the solvent removed. Distillation of the residue gave 63.4 grams (81% of theoretical yield) of liquid 2-bromo-1,4-dimethoxy-naphthalene (boiling 200°–210° at 0.1 mm Hg). The product has a nuclear magnetic resonance spectrum consistant with the expected structure and has peaks expressed in parts per million relative to tetramethylsilane at 8.0 (m,2H), 7.4(m,2H), 6.9(s,1H), 3.9(d,6H).

A solution of 15.0 grams (0.056 mol) of the above 2-bromo-1,4dimethoxynaphthalene in 300 ml of tetrahydrofuran, prepared under anhydrous conditions, is cooled to −78° C. To this is added 35.1 ml of a 1.6M solution of n-butyllithium in hexane. The resulting mixture is stirred 10 minutes and copious amounts (about 30 grams) of powdered dry ice which has been washed in anhydrous ether are added. The reaction mixture is allowed to warm to room temperature; after 3 hours water is added and most of the solvent removed under reduced pressure. The residue is partitioned between ether and 2M sodium hydroxide, the aqueous layer separated, saturated with ammonium chloride, and the pH adjusted to 2 by the addition of 10% aqueous hydrochloric acid. The resulting mixture is extracted three times with ether, the combined organic layers dried over sodium sulfate, and the solvent removed. The residue is crystallized from aqueous methanol to give 11.2 grams, (86%) of 1,4-dimethoxy-2-naphthanoic acid. The white crystalline product melts at 169°–170° C. The nuclear magnetic resonance spectrum is consistent with the expected structure and has peaks at 8.1(m,2H), 7.6(m,2H), 7.15(s,1H), 4.0(d,6H). The product exhibited an infrared spectrum with major absorptions in 2900 cm$^{-1}$ and 1690 cm$^{-1}$.

The 1,4-dimethoxy-2-naphthanoic acid, 14.3 grams (0.06 mol) is dissolved in 50 ml of thionyl chloride and the resulting mixture stirred overnight at room temperature. The excess thionyl chloride is removed under reduced pressure and residue is recrystallized from hexane to give 14.2 grams (94% of theoretical yield) of a green moisture-sensitive crystalline product, melting point 89°–95° C. The nuclear magnetic resonance spectrum is consistent with the expected structure and has peaks at 8.2(m,2H), 7.8(m,2H), 7.2(s,1H), 4.0(d,6H).

To 0.004 mole of n,n-dimethylethylenediamine and 0.004 mole of triethylamine, in 50 ml of anhydrous tetrahydrofuran is added 1.0 gram (0.004 mol), of 1,4-dimethoxy-2-naphthoyl chloride in one portion. A white precipitate is formed and the mixture stirred for three hours. A small amount of water is added, and the solvent removed under reduced pressure. The residue is partitioned between 10% aqueous sodium hydroxide and ether. The organic layer is separated, washed with brine, dried over potassium bicarbonate and solvent removed. The residue is dissolved in anhydrous ether and a slow stream of hydrogen chloride gas bubbled through the mixture for 10 minutes. The product is collected and recrystallized from chlorform-hexane as a white crystal product having a melting point of 93°–95° C. The product is sparingly soluble in water and in ethyl alcohol. An elemental analysis for 1,4-dimethoxy-N-(2-dimethylaminoethyl)-2-naphthalene carboxamide hydrochloride: calculated C:60.26%, H:6.79%, N:8.27%, found: C:59.90%, H:7.12%, N:7.91%. The NMR spectrum is determined and found to be consistent with the expected structure having peaks at 8.05 (m,2H), 7.4(m,3H), 3.95(s,3H), 3.8(s,3H), 3.6(q,2H), 2.5(t,2H), 2.2(s,6H).

EXAMPLE 2

This example illustrates the preparation of another typical 1,4-dimethoxynaphthalene carboxamide of this invention.

1,4-Dimethoxy-2-naphthanoyl chloride is prepared exactly as described in Example 1. To 0.004 mol of 1,1-dimethyl-1,3-propylenediamine and 0.004 mol, of triethylamine in 50 ml of anhydrous tetrahydrofuran is added 1.0 gram, 0.004 mol of 1,4-dimethoxy-2-naphthanoyl chloride in one portion. A white precipitate is formed and the mixture stirred for three hours. A small amount of water is added and the solvent removed under reduced pressure. The residue is partitioned between 10% aqueous sodium hydroxide and ether. The organic layer is separated, washed with brine, dried over potassium carbonate and the solvent removed. The residue is dissolved in anhydrous ether and a slow stream of hydrogen chloride gas is bubbled through the mixture for 10 minutes. The product is collected by filtration and recrystallized from chlorform-hexane to give a white crystalline compound having a melting point of 89°–90° C. The product is sparingly soluble in water and ethyl alcohol. Elemental analysis is conducted for the compound 1,4-dimethoxy-N-(3-dimethylaminopropyl)-2-naphthalenecarboxamide hydrochloride, the calculated values are C:60.50%, H:6.86%, N:7.80%, found: C:60.56%, H:7.25%, N:7.80%. The NMR spectrum is consistent with the expected structure having peaks at 8.1(m,2H), 7.4(m,3H), 4.05(s,3H), 3.95(s,3H), 3.80(q,2H), 2.4(multiplicity and integration obscured by neighboring peak), 2.3(s, integration obscured by neighboring peak), 1.95(t,2H).

EXAMPLES 3 & 4

These examples illustrate the use of the compounds described in Examples 1 and 2 in suppressing convulsions induced in mice by supramaxal shock.

Male albino ICR-swiss mice fasted for 5–6 hours and weighing 20–26 grams are used in all procedures. The compounds of the Examples 1 and 2 are dissolved in water and administered in dosages of 0.01 cc per gram body weight to groups of twelve mice via oral gavage at the milligrams per kilograms per body weight in the table below. One hour after administration of the compound, the mice are given a transcranal electroshock, 60 hertz, 25 milliamps of 0.2 second duration. This stimulus is approximately 3 times the current required to produce tonic flexion-extension convulsions in 100% of the control mice tested. The animals are then observed, and the number undergoing convulsion noted. When the $ED_{50}$ is bracketed (at least one dose above and one dose below), an estimate of the $ED_{50}$ is calculated. The acute $LD_{50}$ is determined as follows: Groups of four mice each are given selected doses of the test compound and placed in plastic cages with food and water ad lib. Twenty-four hours later, the number of dead mice is noted. When the $LD_{50}$ is bracketed (at least one dose above and one below) an estimate of the $LD_{50}$ is calculated. The results of the tests are averaged and tabulated in Table 1. The values for Valproic acid and Dilantin are included in the table for comparison.

| Compound | Supramaximal Electroshock Antagonism Approximate $ED_{50}$ Mg/Kg | Acute (24 hr.) Toxicity Approximate $LD_{50}$ Mg/Kg | Approximate Safety Ratio $LD_{50}/ED_{50}$ |
|---|---|---|---|
| 1,4-Dimethoxy-N—(2-dimethylaminoethyl)-2-naphthalenecarboxamide hydrochloride | 45 | 750 | 17 |
| 1,4-Dimethoxy-N—(3-dimethylaminopropyl)-2-naphthalenecarboxamide hydrochloride | 75 | 750 | 10 |
| Valproic Acid | 600 | 1,425 | 2.4 |
| Dilantin | 13 | 417 | 32 |

What we claim and desire to protect by Letters Patent is:

1. A sustained release composition comprising microparticles having a size below 20 microns of an agent comprising 1,4-dimethoxy naphthalenecarboxamide having the general formula

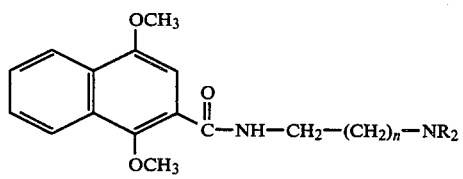

wherein R is selected from the group consisting of methyl, ethyl and propyl groups and n is a whole number from 1 to 2 and its nontoxic salts, microencapsulated in a solid protective coating of a cellulose ether.

2. The composition of claim 1 where the microcapsules are compressed into tablets.

3. The composition of claim 1 where the cellulose ether is ethyl cellulose.

4. A method for suppressing seizures and convulsions which comprises administering to a person prone to having seizures or convulsions and in need of such treatment a pharmaceutically effective amount of an agent comprising 1,4-dimethoxy naphthalenecarboxamide having the general formula

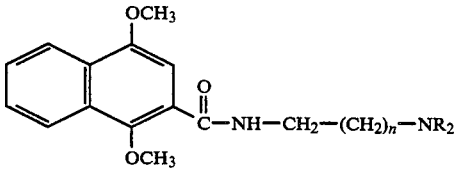

wherein R is selected from the group consisting of methyl, ethyl and propyl groups and n is a whole number from 1 to 2 and its nontoxic salts.

5. The method of claim 4 where said administration is oral administration.

6. The method of claim 4 where said 1,4-dimethoxy naphthalenecarboxamide is microencapsulated and compressed into tablets.

* * * * *